United States Patent
Murakami et al.

(10) Patent No.: US 7,808,256 B2
(45) Date of Patent: Oct. 5, 2010

(54) ELECTRICAL RESISTANCE MEASURING DEVICE FOR TIRES, AND METHOD THEREOF

(75) Inventors: Kosei Murakami, Kodaira (JP);
Norimichi Uchida, Kodaira (JP);
Takahiro Goto, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 187 days.

(21) Appl. No.: 11/914,523

(22) PCT Filed: Apr. 11, 2006

(86) PCT No.: PCT/JP2006/307632

§ 371 (c)(1),
(2), (4) Date: Nov. 15, 2007

(87) PCT Pub. No.: WO2006/123488

PCT Pub. Date: Nov. 23, 2006

(65) Prior Publication Data

US 2009/0072842 A1    Mar. 19, 2009

(30) Foreign Application Priority Data

May 16, 2005    (JP) .............................. 2005-142390

(51) Int. Cl.
*G01R 27/08* (2006.01)
(52) U.S. Cl. ......................................... 324/691; 73/146
(58) Field of Classification Search .................. 324/691
See application file for complete search history.

(56) References Cited

U.S. PATENT DOCUMENTS

| | | | | |
|---|---|---|---|---|
| 4,336,496 A * | 6/1982 | Schnabl et al. | ............... | 324/758 |
| 5,111,687 A * | 5/1992 | Hill | .............................. | 73/146 |
| 5,898,047 A * | 4/1999 | Howald et al. | ........... | 152/152.1 |
| 7,204,135 B2 * | 4/2007 | Robert | ......................... | 73/146 |
| 2002/0166372 A1* | 11/2002 | Farne | ........................... | 73/146 |
| 2003/0188574 A1* | 10/2003 | Weiss | ........................... | 73/146 |

FOREIGN PATENT DOCUMENTS

| | | | |
|---|---|---|---|
| JP | 02-124474 A | | 5/1990 |
| JP | 2000-009771 | * | 1/2000 |
| JP | 2000-009771 A | | 1/2000 |
| JP | 2002-096402 A | | 4/2002 |

\* cited by examiner

*Primary Examiner* — Timothy J Dole
*Assistant Examiner* — Benjamin M Baldridge
(74) *Attorney, Agent, or Firm* — Sughrue Mion, PLLC

(57) ABSTRACT

To provide a resistance measuring device not requiring a long time for the resistance measurement work of a tire and maintaining the accuracy of measurement to assure the electrical conductivity characteristics of the tire and a method thereof.

An electrical resistance measuring device for tires 10 comprises first and second probes 2, 3 for measuring an electrical resistance value of a tire 5, wherein the first probes 2 abut on a plurality of portions in an outer peripheral surface of a tread part 6 and the second probe 3 abuts on a periphery of a center part of a tire 5, and thereby an electrical resistance value between the tread part 6 and the bead part 9 is measured.

17 Claims, 2 Drawing Sheets

ELECTRICAL RESISTANCE MEASURING DEVICE FOR TIRES, AND METHOD THEREOF

TECHNICAL FIELD

The present invention relates to electrical resistance measuring devices for tires that measure the electrical resistance of a tire compounding conductive rubber in tread rubber, and a method thereof.

BACKGROUND ART

Conventionally, a low electrically conductive material, such as silica, is compounded in rubber of a tire in order to improve rolling resistance of the tire. This improves the rolling resistance of the tire, but on the other hand increases an electrical resistance value of tread rubber, thus causing a problem that static electricity generated on a vehicle is hardly discharged to a road surface. Then, a method has been employed, in which one sheet of tread rubber layer made by compounding conductive rubber in the tread rubber is applied to a forming drum, thereby manufacturing a tire, and in this method the electrical resistance value of the tread rubber layer is measured before forming. In order to increase the accuracy of measurement of the electrical resistance value, the number of times of measurement needs to be increased, and therefore the working efficiency in the measurement is poor.

In recent years, in place of the above-described manufacturing method of tires, a method of forming the tread by laminating a ribbon-shaped tread rubber onto the molding drum is used, and a tire is produced, which secures electrical conductivity without deteriorating the rolling resistance by laminating a ribbon-shaped tread rubber composed of a low electrically conductive rubber onto an area except the middle portion in the width direction of the tread part and the side face of the tread part and then by laminating a high electrically conductive rubber ribbon onto the middle part and the side face (see Patent Document 1).

However, in this tire with the high electrically conductive rubber ribbon laminated thereon, it is impossible to measure the electrical resistance value in a manner similar to that of the conventional tire manufacturing method of applying the tread rubber layer onto the molding drum. This is because in the conventional tire manufacturing method a place to be measured is one sheet of tread rubber layer while in the recent tire manufacturing method an elongated high electrically conductive ribbon is the target to be measured, and therefore with the conventional measuring method, the number of measured places becomes huge, thus decreasing the working efficiency and also making it difficult to increase the accuracy of measurement.

Moreover, other known conventional electrical resistance measuring devices of tires include the one in which an electrical resistance measuring device is attached to a pair of first and second probes, which are to be pressed against the bead part and tread part of a tire, via electric cords (see Patent Document 2). In this electrical resistance measuring device, when measuring the electrical resistance value of a product tire, the following work is repeated to increase the accuracy of measurement; that is, the pair of first and second probes is abutted against a tire and the electrical resistance value is measured, and thereafter the both probes are detached from the tire and then the tire is rotated slightly at a low speed, and subsequently the rotation is stopped and the both probes are abutted against the tire and the measurement is made. However, this measurement work takes a long time.

[Patent Document 1] Japanese Patent Application Laid-open No. 2002-96402
[Patent Document 2] Japanese Patent Application Laid-open No. 2000-9771

DISCLOSURE OF THE INVENTION

Problems to be Solved by the Invention

The problem of the present invention is to provide a resistance measuring device and a method thereof which do not require a long time for the resistance measurement work of a tire and which further maintain the accuracy of measurement and assure the electrical conductivity characteristics of the tire.

In order to solve the above-described problem, according to the present invention of claim 1, an electrical resistance measuring device for tires comprises a first and second probes for measuring an electrical resistance value of a tire, wherein the first probes abut on multiple portions in an outer peripheral surface of a tread part, the second probe abuts on a periphery of a center part of the tire, and thereby an electrical resistance value between the tread part and a bead part is measured.

According to the invention of claim 2, in the electrical resistance measuring device for tires according to claim 1, a contact surface of the first probe has substantially the same shape as that of the outer peripheral surface of the tire.

According to the invention of claim 3, in the electrical resistance measuring device for tires according to claim 2, the second probe abuts on a position of a center part of a disc wheel, whereby an electrical resistance value between the tread part and the bead part is measured via a tire rim.

According to the invention of claim 4, the electrical resistance measuring device for tires according to claim 1 further comprises a rotation means for bringing a tip part of the second probe into contact with a bead part to rotate the second probe, and thereby measuring an electrical resistance value between the tread part and the bead part.

According to the invention of claim 5, the electrical resistance measuring device for tires according to claim 1 further comprises a rotation means for bringing a plurality of first probes into contact with a plurality of portions of the outer peripheral surface of the tread part, and bringing a tip part of the second probe into contact with the bead part, and thereby supporting and rotating the tire, wherein an electrical resistance value between the tread part and the bead part is measured.

According to the invention of claim 6, an electrical resistance measuring method for tires includes the steps of:
bringing a probe into contact with a plurality of portions of an outer peripheral surface of a tread part;
bringing one second probe into contact with a periphery of a center part of a tire; and
measuring an electrical resistance value of the tire.

According to the invention of claim 7, in the electrical resistance measuring method for tires according to claim 6, the step of measuring an electrical resistance value of the tire includes bringing the second probe into contact with a center part of a disc wheel.

According to the invention of claim 8, in the electrical resistance measuring method for tires according to claim 6, the step of measuring an electrical resistance value of the tire includes bringing the second probe into contact with a bead part to measure while rotating the second probe.

According to the invention of claim 9, in the electrical resistance measuring method for tires according to claim 6, the step of measuring an electrical resistance value of the tire includes bringing the second probe into contact with a bead part to measure while rotating the tire.

Advantageous Effects of the Invention

An electrical resistance value between a tread part and a bead part can be measured automatically, and moreover, the accuracy of measurement can be maintained. The electrical conductivity characteristics of a tire can be assured and the measurement work can be simplified significantly.

Figure 1:
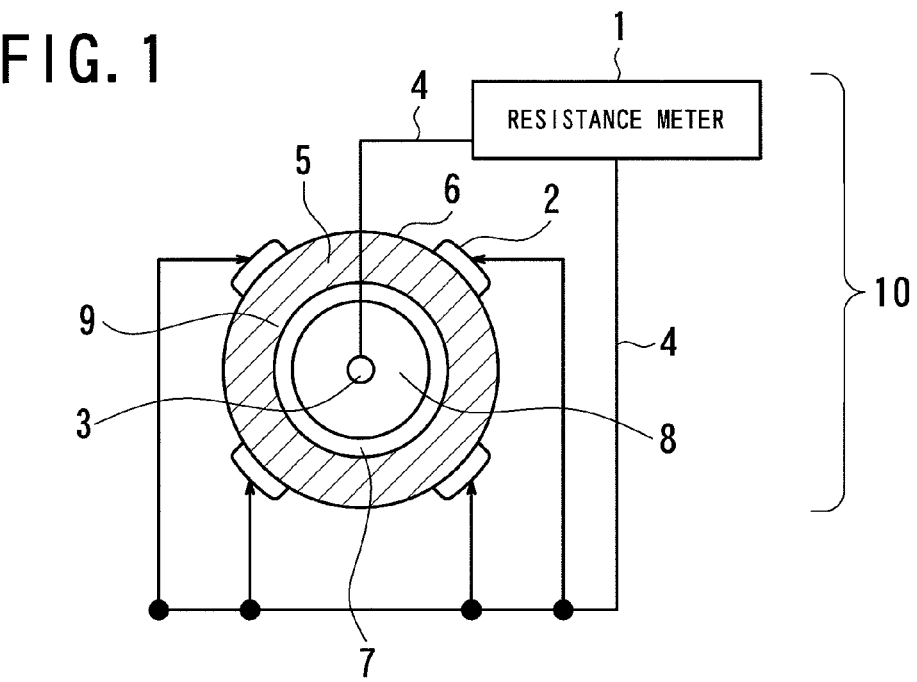
FIG. 1 is a conceptual diagram showing the entire configuration of a first embodiment of the present invention.

DESCRIPTION OF THE REFERENCE SYMBOLS 1 resistance meter
2 first probe
3 second probe
4 electric cord
5 tire
6 tread part
7 rim part
8 disc wheel
9 bead part
10 electrical resistance measuring device for tires

BEST MODES FOR CARRYING OUT THE INVENTION

With reference to FIG. 1, a conceptual diagram showing the entire configuration of a first embodiment is described. Reference numeral 10 of FIG. 1 represents an electrical resistance measuring device for tires that includes a resistance meter 1, four first probes 2 arranged around a tread part 6 of a tire 5, a second probe 3, and an electric cord 4. The electric cord 4 is connected to the first and second probes 2 and 3, and other end thereof is connected to the resistance meter 1. As the quality of the material of the first and second probes 2 and 3, it is desirable to use a material with a low resistivity and a low degree of hardness. In addition, reference numeral 5 represents the tire, 6; the tread part, 7; the rim part, 8; the disc wheel, and 9; the bead part.

The contact surface of the first probe 2 is set to have substantially the same shape as that of the outer peripheral surface of the tread part 6 of the tire. For a tire having a high electrically conductive rubber ribbon only in a middle portion in the width direction of the tread part, the first probe 2 is abutted against a middle portion in the width direction of the tread part 6, while for a tire having a high electrically conductive rubber ribbon in a side face in the width direction of the tread part 6, the first probe 2 is abutted against the entire width of the tread part 6. In addition, in the embodiments described hereinafter, description will be made assuming that for a tire having a high electrically conductive rubber ribbon only in the middle portion, the first probe 2 is abutted against the middle portion of the tread part 6.

It is preferable that the second probe 3 have, for example, a shape with a cylindrical tip part and that the head of the tip part thereof have substantially the same shape as that of the contact surface of a measurement object. The reason that the contact surfaces of the first and second probes 2 and 3 are set in this manner is that by increasing the contact area of the tread part 6, the contact resistance is reduced significantly and the accuracy of measurement of the electrical resistance value is increased.

When measuring the electrical resistance value of the tire 5, the four first probes 2 are abutted against positions where the outer periphery of the tread part 6 is divided substantially equally, preferably against a middle portion of the tread part 6 in the width direction at the four positions where the outer periphery of the tread part 6 is divided substantially equally, and also the second probe 3 is abutted against a position of the center part of the disc wheel 8, and then the electrical resistance meter 1 is powered on. By measuring the electrical resistance value between the tread part 6 and the bead part 9 via the disc wheel 8, the measurement of the electrical resistance value of the tire 5 is made.

By bringing the first and second probes 2 and 3 into contact with the tread part 6 and the disc wheel 8 at such positions, it is possible to measure the electrical resistance values at four places where the four first probes 2 are at almost equal distance to the second probe 3, so that the discharging amount of static electricity that is generated in a tire of a vehicle when the vehicle drives on a road surface can be measured properly.

In the measurement of the electrical resistance value of the tread rubber which is conventionally carried out, only the electrical resistance of a high electrically conductive rubber ribbon existing between a pair of first and second probes 2 and 3 is measured, and it is therefore necessary to rotate the tire 5 at a low speed and measure at a plurality of places, as described above, however, in this embodiment, because the measurement at four places can be made simultaneously, the measurement work can be expedited by just that much.

In addition, the above first embodiment has been described as being provided with the four first probes 2, but not limited to this number, and the more the number of the first probes is, the further the accuracy of measurement is improved.

Figure 2:
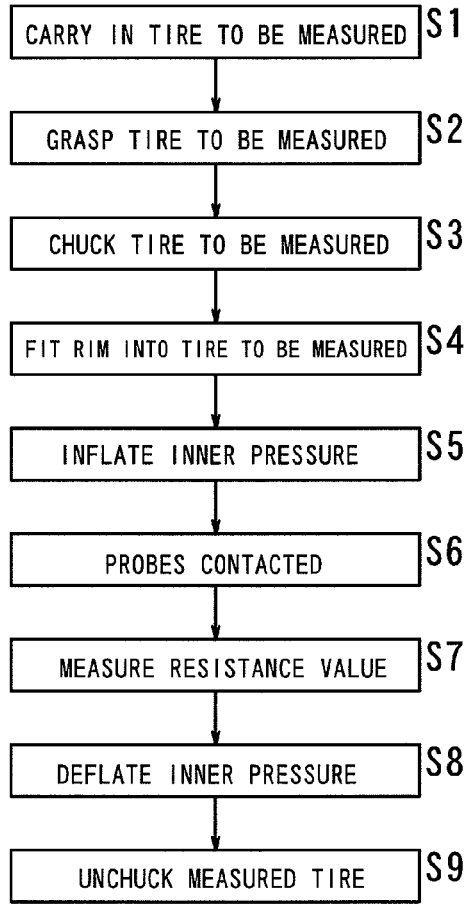
FIG. 2 is a flowchart for measuring an electrical resistance value of a tire from a step of bringing in the tire to be measured, a step of measuring the electrical resistance value of the tire, and to a step of releasing the measured tire.

The procedure for measuring the electrical resistance value of the tire 5 is described with reference to a flowchart shown in FIG. 2. The measurement of the electrical resistance value of the tire 5 is automated using a resistance measurement system for tires. Accordingly, the measurement procedure of the electrical resistance value of the tire 5 described to be below is the one concerning the measurement work by means of the resistance measurement system for tires, and the resistance measurement system for tires itself is conventionally well known, so the description thereof is omitted.

The tire 5 is carried in by a transportation means represented by a belt conveyor (S1), and is then grasped by a robot arm, for example (S2), and is moved to a chucking device for measurement of the electrical resistance value. The tire 5 is held by upper and lower chucking rings of this chucking device (S3). The tire rim 7 is fitted into the held tire 5 (S4), and a compressed air is injected into the tire 5 (inflate internal pressure) via a valve (S5).

The four first probe 2 equipped to, for example, a general holding means are abutted against positions of the center part of the width (width of the tread part 6) of the tire 5, where the outer peripheral surface of the tread of the tire 5 is equally divided into four, and also the second probe 3 similarly equipped to a holding means is abutted against a center part of the outer peripheral surface of the disc wheel 8 (S6). Next, the resistance meter 1 is powered on and the electrical resistance value of the tire 5 is measured (S7). After completion of the measurement, the air of the tire 5 is removed (deflate internal pressure) via the tire valve (S8), and then the measured tire 5 is detached from the chucking device and is transferred to the transportation means (S9).

Figure 3:
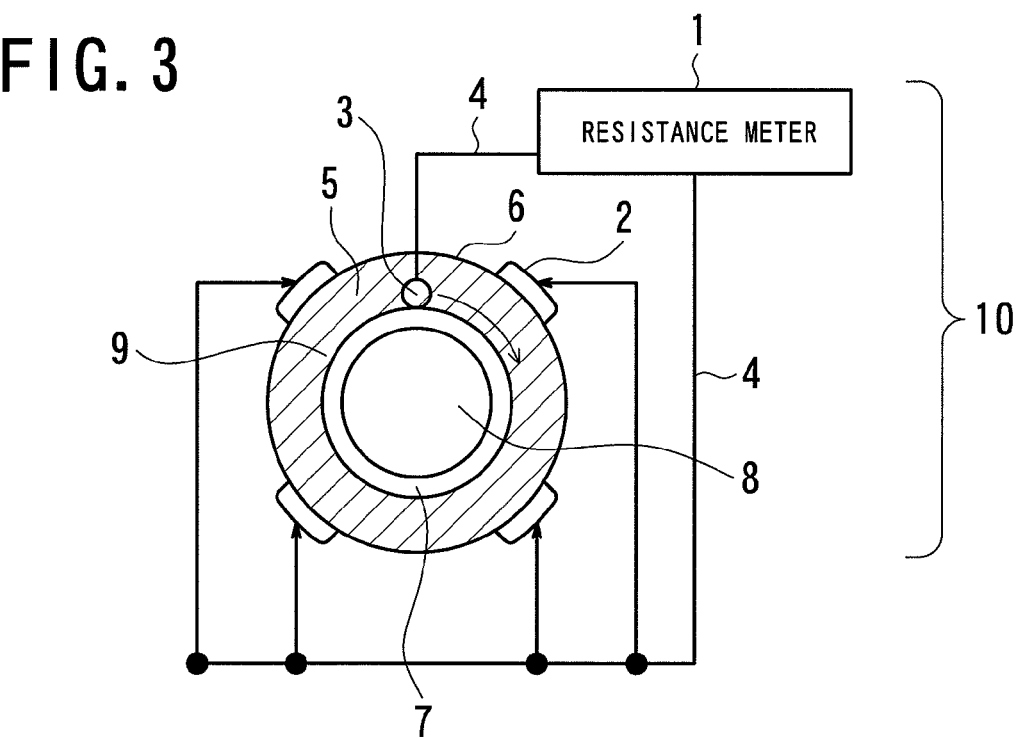
FIG. 3 is a conceptual diagram showing the entire configuration of a second embodiment of the present invention.

With reference to FIG. 3, a conceptual diagram showing the entire configuration of a second embodiment of the present invention is described. The second embodiment differs from the first embodiment in that the second probe 3 equipped to a general rotation means rotates while being abutted against the bead part 9, and the other configuration is the same.

In the procedure for measuring the electrical resistance value of the tire 5 of the second embodiment, only the work procedures of S6 and S7 shown in the first embodiment are different and the other work procedures are the same, so the description thereof is omitted. The four first probes 2 are abutted against center portions of the width (width of the tread part 6) of the tire 5, wherein the outer peripheral surface of the tread of the tire 5 is equally divided into four, and also the second probe 3 equipped to the rotation means is abutted against the side wall of the bead part 9 (S6), and the electrical resistance value between the tread part 6 and the bead part 9 is measured while rotating the second probe 3 one turn as soon as the resistance meter 1 is powered on (S7).

Figure 4:
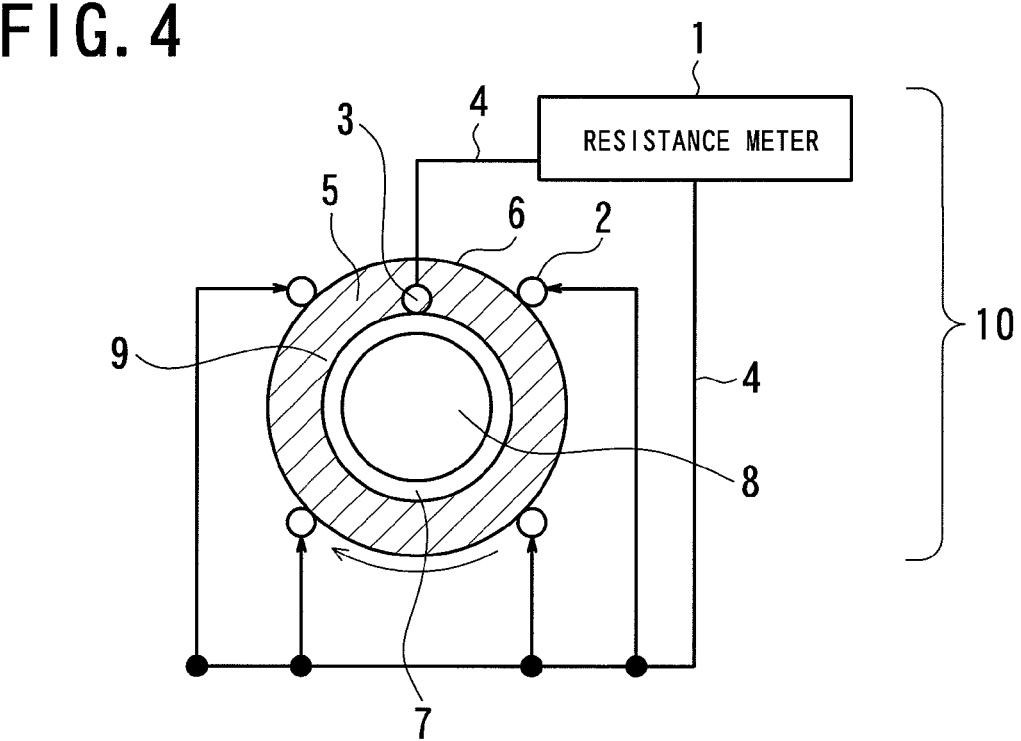
FIG. 4 is a conceptual diagram showing the entire configuration of a third embodiment of the present invention.

With reference to FIG. 4, a conceptual diagram showing the entire configuration of a third embodiment of the present invention is described. In the third embodiment, the same second probe 3 as that of the first and second embodiments is used and the shape of the first probe is cylindrical, for example, and the configuration of the third embodiment differs from that of the second embodiment in that the tire 5 to be measured is made one rotation while the four first probes 2 equipped to a general holding means are abutted against positions parallel to the width direction at positions where the outer periphery of the tread part 6 is divided into multiple portions substantially equally.

The procedure for measuring the electrical resistance value of the tire 5 of the third embodiment is different from that of the first embodiment only in the work procedures of S6 and S7 shown in the first embodiment and the other work procedures are the same, so the description thereof is omitted. The four first cylindrical probes 2 are abutted against center portions of the width (width of the tread part 6) of the tire 5, wherein the outer peripheral surface of the tread 6 of the tire 5 is equally divided into four, and also the second probe 3 equipped to a general holding means is abutted against the side wall of the bead part 9 (S6), and the electrical resistance value between the tread part 6 and the bead part 9 is measured while the tire 5 to be measured is made one rotation by a general rotation means as soon as the resistance meter 1 is powered on (S7). Incidentally, the reason that the first probe 2 is cylindrical is that the frictional resistance when the tire rotates is reduced.

Although the second and third embodiments differ in whether the second probe 3 rotates or the tire 5 rotates, the method for measuring the electrical resistance value between the tread part 6 and the bead part 9 is the same. In any of the embodiments, when the resistance meter 1 is powered on, as the rotating time elapses, the electrical resistance value between the tread part 6 and the bead part 9 over the entire periphery of the tire will be integrated during one revolution.

Moreover, in the first embodiment and the second and third embodiments, a member serving as a target against which the second probe 3 is abutted is different between the disc wheel 8 and the bead part 9, however, the object of measuring the electrical resistance value between the tread part 6 and the bead part 9 is the same. Accordingly, the member serving as a target against which the second probe 3 is abutted may be any one of the rim part 7, the disc wheel 8, and the bead part 9. Then, a place where the second probe 3 may be abutted against these members is referred to as a "periphery of a center part".

In the above-described first to third embodiments, as a target for measuring the electrical resistance of a tire, a product tire has been described, however, even a green tire can be measured. However, in the case of measuring the green tire, the electrical resistance measuring device for tires of the second and third embodiments will be used, and the procedures except S4, S5, and S8 of the flowchart shown in FIG. 2 will be used as the method of measuring the electrical resistance of the tire.

As described above, the electrical resistance measuring device 10 for tires of the first embodiment can automatically measure the electrical resistance value between the tread part 6 and the bead part 9 instantaneously, and can further maintain the accuracy of measurement. The electrical conductivity characteristics of a tire can be assured and the measurement work can be simplified significantly. Then, the electrical resistance measuring device 10 for tires of the second and third embodiments can automatically measure the electrical resistance value between the tread part 6 and the bead part 9, and can provide the measurement results with high measurement accuracy. In other words, because the electrical resistance measuring device 10 for tires measures the electrical resistance value over the entire periphery of a tire, the discharging amount of static electricity that is generated in a tire of a vehicle when the vehicle drives on a road surface can be measured properly. Moreover, the measurement work can be simplified significantly.

What is claimed is:

1. An electrical resistance measuring device for tires, comprising:

A first plurality of probes and a second probe for measuring an electrical resistance value of a tire, and an electrical resistance meter, wherein the first plurality of probes abut on multiple portions of an outer peripheral surface of a tread part, the second probe abuts on a periphery of a center part of the tire, and thereby an electrical resistance value between the tread part and a bead part is measured by the electrical resistance meter;

wherein the electrical resistance value is a resistance between each of the plurality of first probes and the second probe that is measured simultaneously.

2. The electrical resistance measuring device for tires according to claim 1, wherein a contact surface of each of the plurality of first probes has substantially the same shape as that of the outer peripheral surface of the tire in a circumferential direction.

3. The electrical resistance measuring device for tires according to claim 2, wherein the second probe abuts on a position of a center part of a disc wheel, whereby an electrical resistance value between the tread part and the bead part is measured via a tire rim.

4. The electrical resistance measuring device for tires according to claim 1, wherein a tip part of the second probe is rotatable while in contact with a bead part, thereby measuring an electrical resistance value between the tread part and the bead part.

5. The electrical resistance measuring device for tires according to claim 1, further comprising a rotation means for bringing the plurality of first probes into contact with a plurality of portions of the outer peripheral surface of the tread part, and bringing a tip part of the second probe into contact with the bead part, and thereby supporting and rotating the tire, wherein an electrical resistance value between the tread part and the bead part is measured.

6. The electrical resistance measuring device for tires according to claim 1, wherein the plurality of first probes abut on multiple portions of the outer peripheral surface of a tread part along a circumference of the tire.

7. The electrical resistance measuring device for tires according to claim 6, wherein the plurality of first probes are provided substantially equally along the circumference of the tire.

8. The electrical resistance measuring device for tires according to claim 7, wherein the plurality of first probes are connected in parallel to one another.

9. The electrical resistance measuring device for tires according to claim 1, wherein the plurality of first probes are connected in parallel to one another.

10. An electrical resistance measuring method for tires, comprising the steps of:
Bringing a plurality of first probes into contact with a plurality of portions of an outer peripheral surface of a tread part;
bringing one second probe into contact with a periphery of a center part of a tire; and
measuring an electrical resistance value of the tire, wherein the electrical resistance value is a resistance between each of the plurality of first probes and the second probe that is measured simultaneously.

11. The electrical resistance measuring method for tires according to claim 10, wherein the step of measuring an electrical resistance value of the tire includes bringing the second probe into contact with a center part of a disc wheel.

12. The electrical resistance measuring method for tires according to claim 10, wherein the step of measuring an electrical resistance value of the tire includes bringing the second probe into contact with a bead part to measure while rotating the second probe.

13. The electrical resistance measuring method for tires according to claim 10, wherein the step of measuring an electrical resistance value of the tire includes bringing the second probe into contact with a bead part to measure while rotating the tire.

14. The electrical resistance measuring method for tires according to claim 10, wherein the plurality of first probes abut on multiple portions of the outer peripheral surface of a tread part along a circumference of the tire.

15. The electrical resistance measuring method for tires according to claim 14, wherein the plurality of first probes are provided substantially equally along the circumference of the tire.

16. The electrical resistance measuring method for tires according to claim 15, wherein the plurality of first probes are connected in parallel to one another.

17. The electrical resistance measuring method for tires according to claim 10, wherein the plurality of first probes are connected in parallel to one another.

\* \* \* \* \*